US005756415A

United States Patent [19]

Takahashi et al.

[11] Patent Number: 5,756,415

[45] Date of Patent: May 26, 1998

[54] METHOD OF MAKING A ENZYME IMMOBILIZING CARRIER

[75] Inventors: Joji Takahashi, Tama; Eiji Kanazawa; Yoshitaka Yamashita, both of Kochi; Tomio Kashiwai, Tosa; Hideo Takenaka, Kochi, all of Japan

[73] Assignee: Toyo Denka Kogyo Co., Ltd., Japan

[21] Appl. No.: 466,898

[22] Filed: Jun. 6, 1995

Related U.S. Application Data

[62] Division of Ser. No. 263,239, Jun. 21, 1994, Pat. No. 5,614,401.

[30] Foreign Application Priority Data

| | | | |
|---|---|---|---|
| Jun. 23, 1993 | [JP] | Japan | 5-177318 |
| Dec. 27, 1993 | [JP] | Japan | 5-350769 |

[51] Int. Cl.$^{6}$ ...... B01J 21/16

[52] U.S. Cl. ...... 502/81; 502/80; 502/83; 502/85; 502/87

[58] Field of Search ...... 502/80, 81, 85, 502/83, 87

[56] References Cited

U.S. PATENT DOCUMENTS

| | | | |
|---|---|---|---|
| 2,477,664 | 8/1949 | Shabaker | 502/81 |
| 4,323,650 | 4/1982 | Rosevear | 435/174 |
| 4,748,121 | 5/1988 | Beaver et al. | 435/176 |

FOREIGN PATENT DOCUMENTS

| | | | |
|---|---|---|---|
| 2726188 | 8/1978 | Germany | 435/176 |
| 1296975 | 11/1989 | Japan . | |
| 2131578 | 5/1990 | Japan | 435/176 |
| 3266985 | 11/1991 | Japan | 435/176 |
| 1833393 | 6/1992 | Japan . | |

*Primary Examiner*—Steven Bos
*Assistant Examiner*—Thomas G. Dunn, Jr.
*Attorney, Agent, or Firm*—Joseph W. Berenato

[57] ABSTRACT

A method of preparing an enzyme immobilizing carrier includes the steps of providing a material consisting of kaolin mineral. The material is subject to acid treatment with a strong acid having a pH of 4 or less, and hydrothermal treatment at a temperature of from about 100° C. to about 250° C. The material is dried, thereby producing a porous powder. The porous powder is baked at a temperature of from about 350° C. to about 1000° C., for thereby producing the carrier.

10 Claims, 4 Drawing Sheets

DIFFERENTIAL PORE CAPACITY (cc/g • log A)
4.0
3.0
2.0
1.0
0.0
pH = 0.5
pH = 1.0
pH = 2.0
pH = 4.0
pH = 6.0
102
103
PORE DIAMETER (Å)

DIFFERENTIAL PORE CAPACITY (cc/g • log A)
4.0
3.0
2.0
1.0
0.0
120
150
180
200
220
REACTION TEMP. (°C)

METHOD OF MAKING A ENZYME IMMOBILIZING CARRIER

This is a division of application Ser. No. 08/263,239, filed Jun. 21, 1994 now U.S. Pat. No. 5,614,401 .

BACKGROUND OF THE INVENTION

1. Field of the Invention

The present invention relates generally to an enzyme immobilizing carrier which is used as a bioreactor, biosensor, filter, and so on to facilitate various biochemical reactions in an industrial field which employs various enzymes as a biological catalyst. More particularly, the present invention relates to a porous powder material to produce such enzyme immobilizing carrier, especially a porous carrier. Furthermore, the present invention relates to a method of producing such porous powder material.

2. Description of the Prior Art

In order to execute various biochemical reaction in an industrial field by using an organic catalyst, for example an enzyme catalyst, many researches and studies on an enzyme immobilized bioreactor and a biosensor have been actively carried out in recent years. On the same occasion, studies on an enzyme immobilizing carrier which is applied to these bioreactor and biosensor have been also progressed. Such the enzyme immobilized bioreactor includes a column which is filled with an organic catalytic material made of an enzyme immobilized carrier. For the carrier, various materials may be used, for example high molecular organic materials such as cellulose, agarose, chitin, carrageenan, poly acrylamide, and inorganic materials such as commonly used porous glass, ceramics, and so on.

However, such the organic materials are apt to have a poor mechanical strength, and mostly require a high temperature treatment in order to prevent the contamination of various germs in a reaction system employing the above described enzyme immobilizing carrier. The organic materials are easily affected by such the high temperature treatment so that their mechanical and chemical properties after the treatment will become unstable. Particularly in a case of mass production system, such the organic material carrier will be remarkably compressed by various pressures, and therefore the compressed carrier will cause fluctuation in reactant flow and pressure. This fluctuation will not perform reaction at a constant rate.

On the other hand, the above described porous glass is possessed of an excellent thermal stability and pores having the diameter range of several hundreds angstroms, while its manufacturing process is complicated and requires a fusing step at a high temperature (about 1500° C.) thereby increasing manufacturing cost. This costly process may not be applied to a commercially available plant for lack of economical profit.

When the carrier is produced by a generally used ceramics material such as alumina and zirconia, such the ceramics carrier has superior thermal and chemical stabilities, but less pores having the diameter range of several hundreds to thousands angstroms which are necessary to immobilize enzyme. Thus the reaction plant employing this ceramics carrier may produce a small amount of the immobilized enzyme and need a relatively large scale and a long reaction period.

Some conventional arts have been proposed to overcome the above described problems caused by using the ceramics carrier For example, Japanese Patent Application Laid-Open Publication No. 63-91083/1988 discloses one typical process that some amount of sepiolite as a raw material are ground into grains having a constant particle size, and then the grains are heated at the temperature range of 800° C. to 1000° C. to form a sepiolite based enzyme immobilizing carrier, hereinafter this will be referred to "sepiolite carrier". Thus produced sepiolite carrier has various merits such as an excellent thermal stability, and many pores having the diameter range of several hundreds to thousands angstroms which are necessary to immobilize enzyme. These pores ensure to improve the capability of enzyme immobilizing function in comparison with the above described ceramics carrier.

Although the sepiolite carrier has the above described merits, the pores are difficult to control their distribution and amount. In addition to this problem, the sepiolite raw material contains some impurities such as carbonate minerals, for example dolomite ($CaCO2.MgCO3$). Since the sepiolite crystals may be broken by any acid treatments for removing the impurities, these alkaline impurities can not be completely removed from the produced sepiolite carrier. When the sepiolite carrier is used as the bioreactor, the alkaline impurities may be eluted under a specific condition and the eluted alkaline components may disturb the biochemical reaction.

BRIEF SUMMARY OF THE INVENTION

Therefore, it is an object of the present invention to provide an improved porous powder adapted for a porous carrier to immobilize enzyme which overcomes the above described conventional problems.

Another object of the present invention is to provide an improved porous powder adapted for a porous carrier to immobilize enzyme, which can control the amount of pores.

An additional object of the present invention is to provide an improved porous powder adapted for a porous carrier to immobilize enzyme, which has a sharp and uniform distribution of pores.

A further object of the present invention is to provide an improved porous powder adapted for a porous carrier to immobilize enzyme, which can satisfy thermal stability, chemical stability and economical profit.

Still another object of the present invention is to provide an improved porous powder adapted for a porous carrier to immobilize enzyme, which has a high capability to generate enzyme activity and is free from compression.

A further object of the present invention is to provide a method for producing the above described porous powder.

To accomplish the above described objects, the porous powder adapted for a porous carrier to immobilize enzyme is produced by the following treatments. Kaolin mineral is added with a strong acid, and subjected to a hydrothermal treatment and a baking treatment.

The method to produce the objective porous powder includes a first step for adding a strong acid to kaolin mineral, a second step for applying a hydrothermal treatment to the resulted material from the first step, a third step for washing and drying the resulted material from the second step to make powder material, and a fourth step for baking the powder material under predetermined conditions to form the porous powder having a uniform pore distribution and a high pore ratio adapted for a porous carrier to immobilize enzyme. Alternatively, the method to produce the objective porous powder includes a first step for adding a strong acid to kaolin mineral, a second step for applying a hydrothermal treatment to the resulted material from the first step, a third step for granulating the slurry or powder resulted from the second step to form granular materials, and a fourth step for baking the granular materials under predetermined conditions to form the porous powder having a uniform pore distribution and a high pore ratio adapted for a porous carrier to immobilize enzyme.

The kaolin mineral to be used in the above described methods is selected from natural minerals or synthetic minerals which are mainly composed of at least one of kaolinite, dickite, nacrite, and halloysite. The strong acid to be used in the above described methods is selected from inorganic acids or organic acids which can provide pH 4.0 or less when the kaolin mineral is soluted by the strong acid into a 10% slurry. The hydrothermal treatment is carried out under the conditions that the treatment temperature is 100° C. or more, preferably 100° to 250° C., more preferably 120° to 200° C.; and the treatment period is for 1 hour or more. The baking temperature after the hydrothermal treatment is 350° to 1000° C.

The particle size of the slurry or powder after the hydrothermal treatment is from several tens μm to several mm. The granulating step is carried out by using any one selected from a rotary granulating method, a spray drying granulating method, a stirring granulating method, a vacuum drying granulating method, a flowing layer granulating method, and so on.

The method of the present invention is based on the conventional knowledge that pores are formed under a specific temperature condition during the baking treatment on kaolin mineral. In this method, alkaline impurities can be completely removed from the kaolin mineral by the strong acid treatment. After the alkaline impurities were removed, the kaolin mineral is subjected to thermal treatments of the hydrothermal and baking treatments to form pores in a sharp and uniform distribution and within a required amount range. That is, the strong acid treatment ensures to provide chemical stability, and both the hydrothermal and baking treatments ensure to provide thermal stability and realize a porous carrier manufacturing process with an economical profit.

When the treating temperature of the hydrothermal treatment is less than the above described range, the pore ratio will be less than the required amount, on the other hand, when it is higher than the range, the kaolin mineral will be decomposed and energy cost will be increased. As disclosed above, the suitable temperature range is 100° to 250° C., preferably 120° to 200° C. for one hour or more.

If the baking temperature is lower than 350° C., water will not be fully discharged from the kaolin crystal and thus the kaolin mineral will not be fully changed into metakaolin. This will cause less pore ratio. If it is higher than 1000° C., the kaolin mineral will be shrunk so that pores will not be fully formed. The above mentioned method will provide the required pore amount when the baking temperature is within the range of 350° to 1000° C.

Other and further objects of this invention will become obvious upon an understanding of the illustrative embodiments about to be described or will be indicated in the appended claims, and various advantages not referred to herein will occur to one skilled in the art upon employment of the invention in practice.

DETAILED DESCRIPTION OF THE PREFERRED EMBODIMENTS

Figure 1:
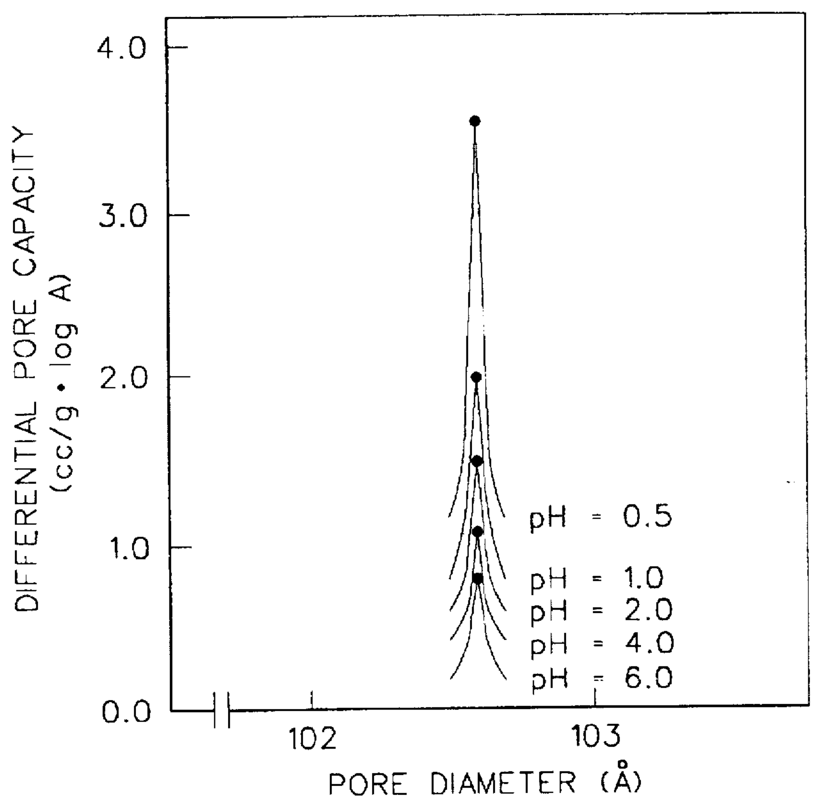
FIG. 1 is a graphical representation which shows the variation of differential pore capacity of produced powder material according to the first embodiment of the present invention when pH value of the kaolin mineral slurry is varied and the pore diameter of the kaolin mineral is fixed.

The present invention will be understood by discussing some preferred embodiments to produce porous powder adapted for a porous carrier to immobilize enzyme, and the produced porous powder per se.

As disclosed in the above, the porous powder is basically produced by a strong acid adding treatment, a hydrothermal treatment and a baking treatment. Preferable conditions used in the method according to the present invention will be described in detail.

A raw material for the method of the present invention is a kaolin mineral selected from natural minerals or synthetic minerals which are mainly composed of at least one of kaolinite, dickite, nacrite, and halloysite. For example, kaolinite is a main component of various natural clay minerals which have been conventionally used as the raw material of ceramics, china and porcelain manufactures. Kaolinite contains a lot of alumina component, and shows white, gray or yellow. One of high quality natural clays broadly known as "gairome clay" yielded from Seto, Aichi Prefecture, Japan is composed of some organic materials such as lignite to increase its viscosity. This gairome clay is highly esteemed as the most excellent material for ceramic art.

The strong acid used in the method of the present invention is selected from inorganic acids or organic acids which can provide pH 4.0 or less when the kaolin mineral is soluted by the strong acid into a 10% slurry. For example, hydrochloric acid was used in the embodiment of the present invention.

The hydrothermal treatment is carried out under the condition that the treatment temperature is 100° C. or more, preferably 100° to 250° C., more preferably 120° to 200° C.;

and the treatment period is for 1 hour or more. As disclosed above, when the temperature of the hydrothermal treatment is less than the above described range, the pore ratio will be less than the required amount, on the other hand, when it is higher than the range, the kaolin mineral will be decomposed.

The particle size of the slurry or powder after the hydrothermal treatment is prepared for each purpose by using any type of granulating method selected from a rotary granulating method, a spray drying granulating method, a stirring granulating method, a vacuum drying granulating method, a flowing layer granulating method, and so on. For example, in the case of using the porous carrier stuffed in a bioreactor column, it is desirable to decrease the particle size for increasing the contact surface area of the porous carrier with reactant, while the flow rate of the reactant passing through the bioreactor column becomes worse. When the particle size of the porous carrier is less than 10 μm, such carrier will not be practically used because the reaction speed of the reactant is extremely slow. Accordingly, the particle size of the slurry or powder after the hydrothermal treatment is 10 μm or more, practically selected from the range of several ten μm to several mm in response to the particle size of the reactant to be treated.

Then the granulated materials or the powder materials after the hydrothermal treatment are baked at the temperature range from 350° C. to 1000° C.

According to the data resulted from a differential thermal analysis on the kaolin mineral, water content, existed in the form of OH, in the kaolin mineral is gradually dehydrated at about 400° C. or higher. The data indicated the maximum peak of endothermic reaction at about 600° C. After this maximum peak, the kaolin mineral is changed into metakaolin. At about 970° C. to 1000° C., the data indicated some peaks of exothermic reaction caused by crystallization of γ-alumina or mullite. At higher than 1000° C., the materials were gradually shrunk. In other words, when the baking temperature is lower than 350° C., water is not fully discharged from the kaolin crystal to scarcely change the kaolin mineral into the metakaolin. This results in generating porous material with a poor pore ratio. On the contrary, when the baking temperature is higher than 1000° C., pores are broken by the baking shrink. Also, this results in a poor pore ratio. Consequently, the baking treatment is carried out at 350° C. to 1000° C.

In order to increase the immobilized ratio of enzyme, the surface of the produced carrier is suffered from any suitable silane coupling agent and then glutaraldehyde. Since this is one of conventional immobilizing manners, the other commonly used manners may be also applied. Enzyme can be concentratedly and firmly immobilized to the surface of the porous carrier through covalent bonds.

To easily understand the present invention, several embodiments will be described as follows.

Embodiment 1

Gairome clay (main ingredient; kaolinite) was added with hydrochloric acid to prepare 10% slurry samples having various pH values. These slurry samples were set in a Mohle type cylinder case the inside of which is coated with Teflon, trade name. Then they were placed in a warm wind cyclic dryer at 220° C. for 16 hours (hydrothermal treatment). The slurry samples were taken out of the cylinder case and further subjected to filtering, rinsing, and drying to form porous powder. The formed porous powder samples were baked in an electric oven at 700° C. for 2 hours. The baked powder samples were measured their pore distribution by a mercury pressure charging method. The measured result is shown in FIG. 1.

Referring to FIG. 1, the horizontal axis represents pore diameter (angstrom) and the vertical axis represents differential pore capacity (cc/g.log A). Assuming that the pore diameter of the slurry samples are not varied, the differential pore capacity varied in response to pH values 0.5, 1.0, 2.0, 4.0 and 6.0 are plotted. According to FIG. 1, the sample of pH value 0.5 indicates the maximum pore capacity of about 3.5; the sample of pH value 4.0 indicates the pore capacity of about 1.0; and the sample of pH value 6.0 indicates too small to practical use.

Embodiment 2

In order to clarify the influence of the hydrothermal treatment temperature upon the generation of pores, the 10% slurry samples having pH value of 0.5 prepared in Embodiment 1 were set in the same type cylinder case used in Embodiment 1. Then they were placed in a warm wind cyclic dryer at various temperatures for 16 hours (hydrothermal treatment). The slurry samples were taken out of the cylinder case and further subjected to filtering, rinsing, and drying to form porous powder samples. The powder samples were baked in an electric oven at 700° C. for 2 hours. The baked samples were measured their pore distribution by a mercury pressure charging method. The measured result is shown in FIG. 2.

Figure 2:
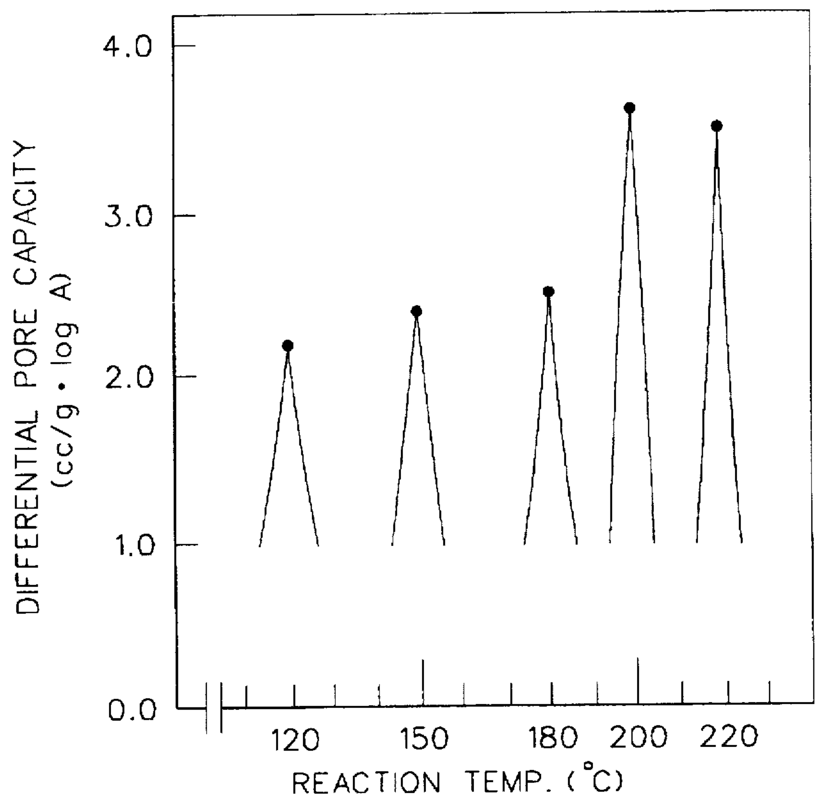
FIG. 2 is a graphical representation which shows the variation of differential pore capacity of produced powder material according to the second embodiment when the reaction temperature of the hydrothermal treatment is varied and pH value of the kaolin mineral slurry is fixed.

Referring to FIG. 2, the horizontal axis represents reaction temperature (°C.)and the vertical axis represents differential pore capacity (cc/g.log A). Assuming that the pH value of the slurry samples are not varied, the differential pore capacity varied in response to various reaction temperatures 120, 150, 180, 200, 220 (°C.) are plotted. According to FIG. 2, the sample treated at 200° C. indicates the maximum pore capacity of about 3.5; the sample treated at 220° C. indicates higher value close to the maximum. In other words, the hydrothermal treatment is preferably carried out at the temperature range from 100° to 220° C., more preferably 120° to 200° C.

Embodiment 3

In order to clarify the influence of the baking temperature upon the generation of pores, the same samples of pH 0.5 prepared as Embodiment 1 were subjected to the hydrothermal treatment at 220° C. for 16 hours, and then baked in the electric ovens controlled at different temperatures for 2 hours. The baked samples were measured their pore distribution by a mercury pressure charging method. The measured result is shown in FIG. 3.

Figure 3:
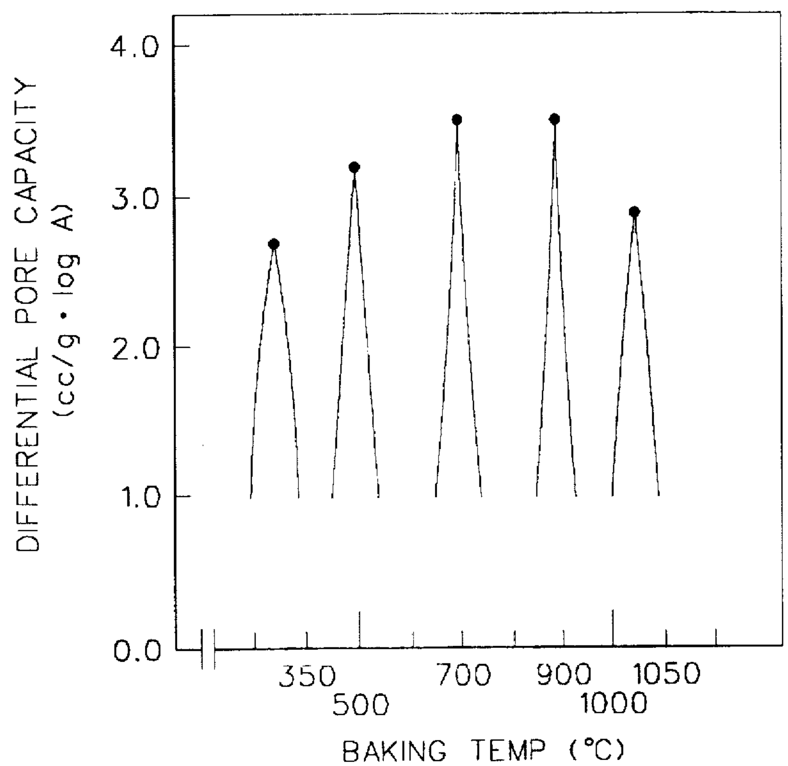
FIG. 3 is a graphical representation which shows the variation of differential pore capacity of produced powder material according to the first embodiment when the temperature of the baking treatment is varied and pH value and the reaction temperature of the kaolin mineral slurry are fixed.

Referring to FIG. 3, the horizontal axis represents baking temperature (°C.) and the vertical axis represents differential pore capacity (cc/g.log A). Assuming that the reaction temperature and pH value of the slurry samples are not varied, the differential pore capacity varied in response to various baking temperatures 350, 500, 700, 900, 1000, and 1050 (°C.) are plotted. According to FIG. 3, the samples treated at 700° and 900° C. indicate the maximum pore capacity of about 3.5; the sample treated at higher than 1000° C. indicates less pore capacity owing to the influence of baked shrinking upon the formed pores. This result proves the baking treatment is preferably carried out at the temperature range from 350° to 1000° C.

Embodiment 4

In order to clarify that the method according to the present invention is superior to one of typically used conventional methods, comparative experiments were carried out. First, the same 10% slurry samples of pH 0.5 prepared as Embodiment 1 were set in the same type cylinder case used in Embodiment 1. Then they were placed in a warm wind cyclic dryer at 220° C. for 18 hours (hydrothermal treatment). The slurry samples were taken out of the cylinder case and further subjected to filtering, rinsing, and drying. One of these samples is subjected to grinding by a sample mill to form a first powder sample. The other samples are granulated by a spray dryer into three granular samples having different three particle sizes. These four samples are baked in an electric oven at 700° C. for 2 hours. The baked samples were called as H-powder (average particle diameter 8 μm) corresponding to the first powder sample, H-50, H-150 and H-250. "H" represents the samples treated by "Hydrothermal treatment". These numbers represent average particle diameter (μm) of the baked granular samples., respectively.

Comparative Example

Next, in order to prepare comparative conventional samples, commercially available gairome clay was treated in the same manner as Example 4 except for the hydrothermal treatment to produce three samples N-50, N-150, and N-250. "N" represents the comparative samples not treated by the hydrothermal treatment. These numbers represent average particle diameter (μm) of the baked granular samples, respectively.

The samples H-powder, H-50, H-150, H-250, N-50, N-150, and N-250 were subjected to the following tests to clarify the differences between the samples produced by the present invention and the conventionally produced samples.

Measurement of Pore Ratio and Pore Distribution

Figure 4:
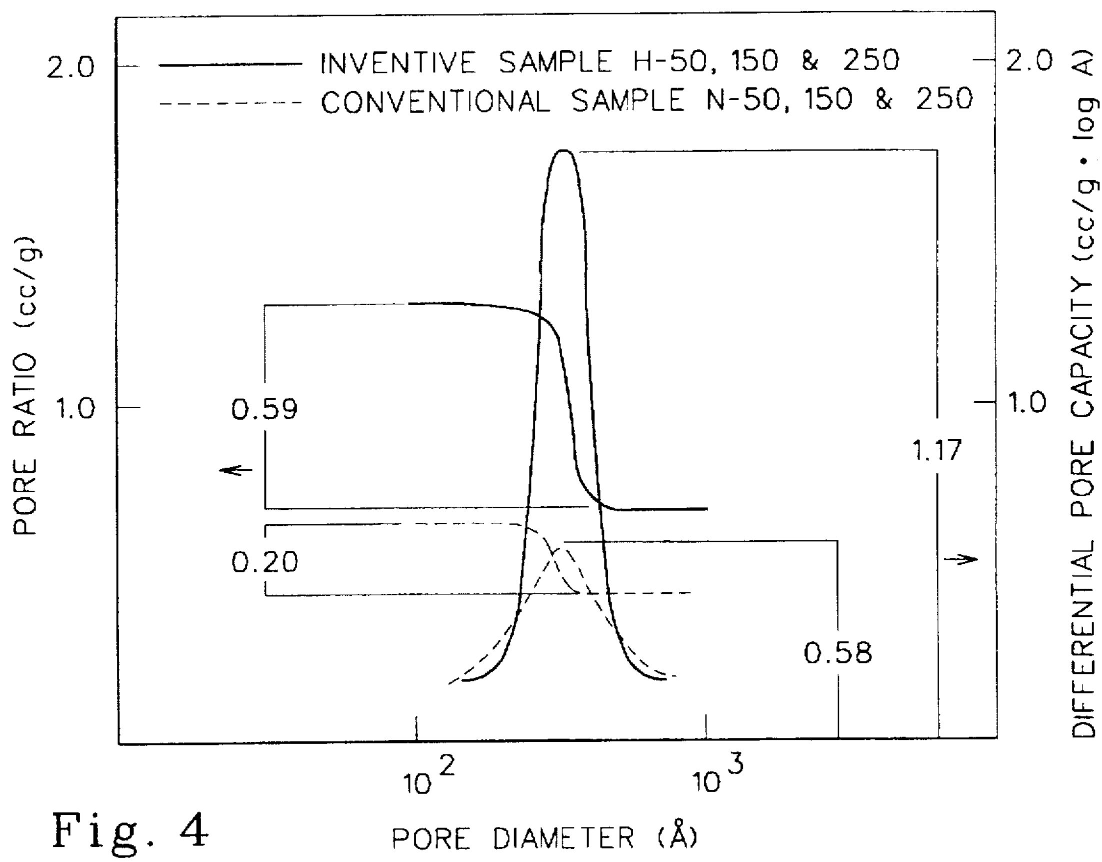
FIG. 4 is a graphical representation which shows the relation between the pore ratio and the differential pore capacity with respect to the pore diameter of the carriers produced by the fourth embodiment according to the present invention and the comparative example.

The samples were measured for their pore distribution by a mercury pressure charging method. The measured result is shown in FIG. 4 which represents the relation between pore ratio (cc/g) and differential pore capacity (cc/g.log A) within the range of pore diameter from $10^2$ to $10^3$ (angstrom). According to FIG. 4, the inventive samples H-50, H-150 and H-250 represented by a solid line show the maximum differential pore capacity of 1.71 and the maximum pore ratio of 0.59, while the conventional samples N-50, N-150 and N-250 represented by a dotted line show the maximum differential pore capacity of 0.58 and the maximum pore ratio of 0.20. In other words, the inventive samples provide the pore distribution curve having a sharp figure and the pore ratio three times as more as the conventional samples. This function does not depend on the particle diameter of the sample.

Measurement of Pressure Loss

Figure 5:
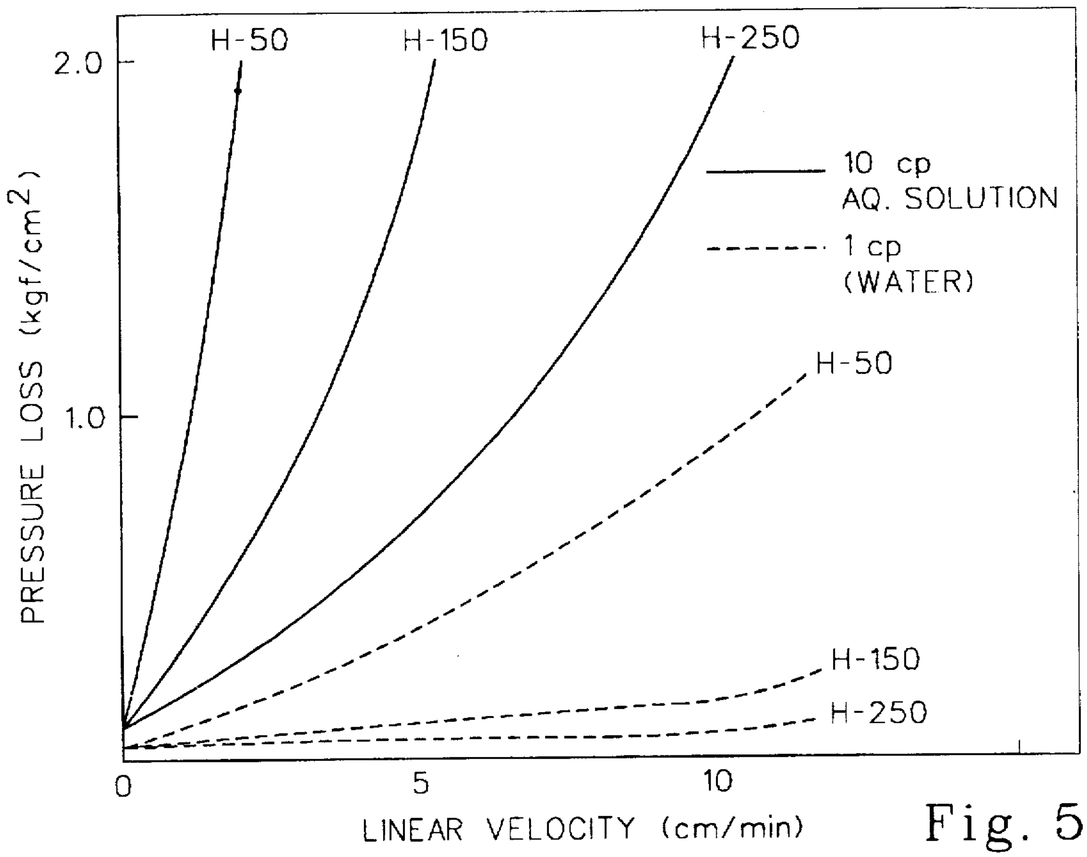
FIG. 5 is a graphical representation which shows the pressure loss generated in various carriers produced by the fourth embodiment according to the present invention.

FIG. 5 shows the pressure loss generated in the inventive porous samples stuffed in a column when reactant is passed through the column. In detail, each 150 cc of the inventive samples H-50, H-150 and H-250 was stuffed into an open column having the inner diameter of 2.8 mm. Two type aqueous solutions having different viscosities, 1 cp and 10 cp, adjusted by glycerol were passed through the columns to measure the pressure loss through there. In FIG. 5, the horizontal axis represents linear velocity (cm/min) and the vertical axis represents pressure loss (kgf/cm$^2$). That is, this data shows the flowed distance per minute of the aqueous solution under various pressures.

According to FIG. 5, the sample H-50 indicates the linear velocity at about 2 cm/min for 10 cp aqueous solution under the pressure of 2.0 kgf/cm$^2$. As larger particle diameter; i.e., the samples H-150 and H-250, their linear velocities are gradually increased. This tendency is also shown for 1 cp aqueous solution (water). On the other hand, although FIG. 5 does not show the data of the sample H-powder having average particle diameter of 8 μm, it was not practically used owing to smaller particle diameter. The low viscous liquid of 1 cp was scarcely passed through the sample H-powder under the pressure of 2.0 kgf/cm$^2$.

Consequently, FIG. 5 proves that the pressure loss is remarkably decreased as the particle diameter of the inventive porous carrier is greater. Especially for higher viscous reactant, the particle diameter of the carrier are preferably greater.

Surface Treatment of Carrier

The samples prepared by Embodiment 4 and Comparative Example were immersed in 2% 3-aminopropyl triethoxisilane soluted in toluene solution to be suffered from silane coupling agent. Then they were rinsed by toluene solution, dried and immersed in 10 mM phosphoric acid buffer solution containing 2.5% glutaraldehyde at 4° C. for 24 hours to be suffered from aldehyde agent.

Immobilization of Oxygen

Each 1 cc of the aldehyde suffered samples was put into an Erlenmeyer flask of 50 cc, and added with 5 cc of 0.1M acetic acid buffer solution, and then placed in an autoclave at 121° C. for 10 min. to be disinfected. After cooling, they were respectively added with 70 mg of glucoamylase and cooled in an ice cooler with stirring for one hour to adsorb and immobilize enzyme to the carrier samples. The enzyme immobilized carrier samples were placed on respective filter papers disinfected, and rinsed 15 times by the above buffer solution to remove non-immobilized enzyme from the carrier samples. For each rinsing operation, 5 cc of the buffer solution was used. The used glucoamylase was originated from Aspergillus niger, manufactured by Bernger Mannheim Yamanouchi Pharmaceutical Co., Ltd.

Measurement of Enzyme Activity

Figure 6:
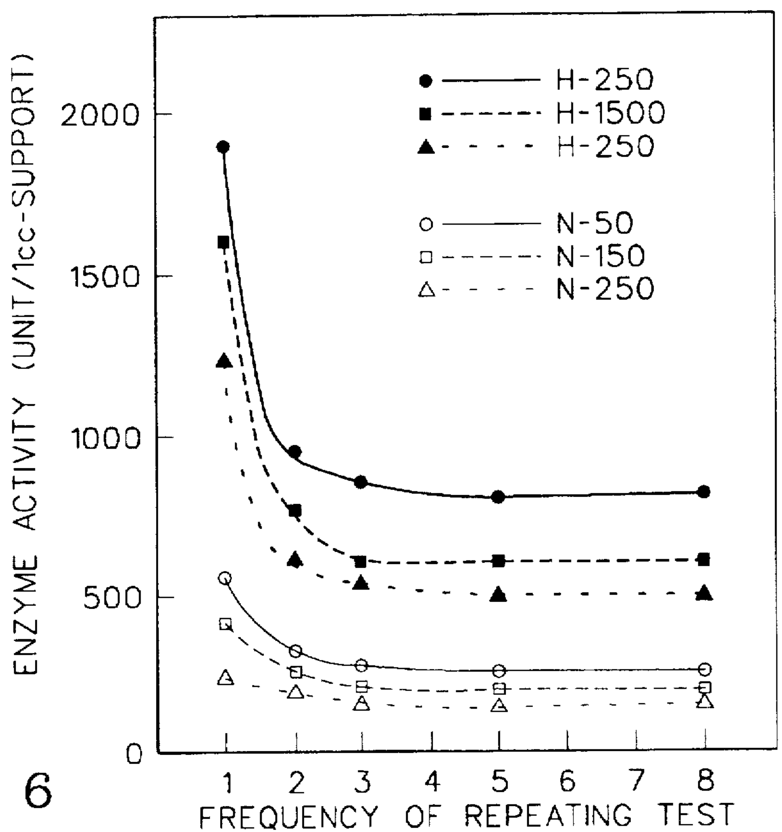
FIG. 6 is a graphical representation which shows the relation between the frequency of repeating test and the enzyme activity with respect to various carriers produced by the embodiment 4 and the comparative example.

In order to carry out the quantitative analysis on the produced enzyme immobilized carrier samples, 10% soluble starch was solved in 0.1M acetic acid buffer solution and disinfected in an autoclave. After cooling, the enzyme immobilized carrier samples were respectively added in 100 cc of the starch solution with stirring at 35° C. to perform the saccharification of the starch solution. During this saccharification process, sampling tests were sometimes carried out to obtain the quantitative analysis of glucose and form their saccharification curves. According to the curves, their respective enzyme activities were obtained by an initial velocity measuring method. Whenever the reaction was completed, only the starch solution was replaced by another and the same reaction was repeated to obtain the data representing the change of enzyme activity. FIG. 6 shows the resulted data. The quantitative analysis of glucose was performed by using Glucose CII-Test Wako, commercial available, produced by Wako Pure Chemical Industries, Ltd.

Referring to FIG. 6, the first and second tests show relatively high enzyme activities because there are some remaining enzymes not immobilized fully. Therefore, the data resulted from the third and later tests are compared with each other. The enzyme activity values of glucoamylase immobilized to the samples H-50, H-150, and H-250 treated with the acid and hydrothermal treatments according to the present invention are appeared within the range of about 500 to 800 Unit per 1 cc of carrier. On the contrary, the values resulted from the conventional samples N-50, N-150 and N-250 without the acid and hydrothermal treatments are appeared within the range of about 150 to 250 Unit/1 cc. This proves that the enzyme activity of the samples produced by the method of the present invention show 3 to 4 times as higher as that of the conventional samples. In addition to this effect, the data shown in FIG. 6 prove the capability of generating enzyme activity is gradually decreased as the particle size of the carrier is reduced. This effect depends on the. contact surface area between the porous carrier and the reactant. The contact surface area of the carrier becomes less in inverse proportion to the particle diameter of the carrier.

In FIG. 6, one Unit of the enzyme activity represents one enzyme unit for generating 1 μmol of glucose per one minute.

Embodiment 5

In order to clarify the influence of the particle size of the carrier, the same slurry sample prepared by the acid and hydrothermal treatments as Embodiment 4 was subjected to a grinding treatment by a sample mill to form a powder sample after rinsing and drying steps. Then the powder sample was granulated by a stirring granulating machine. The granulated sample was baked in an electric oven at 700° C. for 2 hours to form a carrier sample H-1500 having an average particle diameter of 1500 μm. This carrier sample was subjected to a measurement of pressure loss. This measured result shows that the pressure loss of the aqueous solution having the viscosity of 50 cp at the linear velocity of 10 cm/min is 0.2 $kgf/cm^2$ which is substantially equal to that of the sample H-250 prepared in Embodiment 4 for the aqueous solution of 1 cp as shown in FIG. 5.

Figure 7:
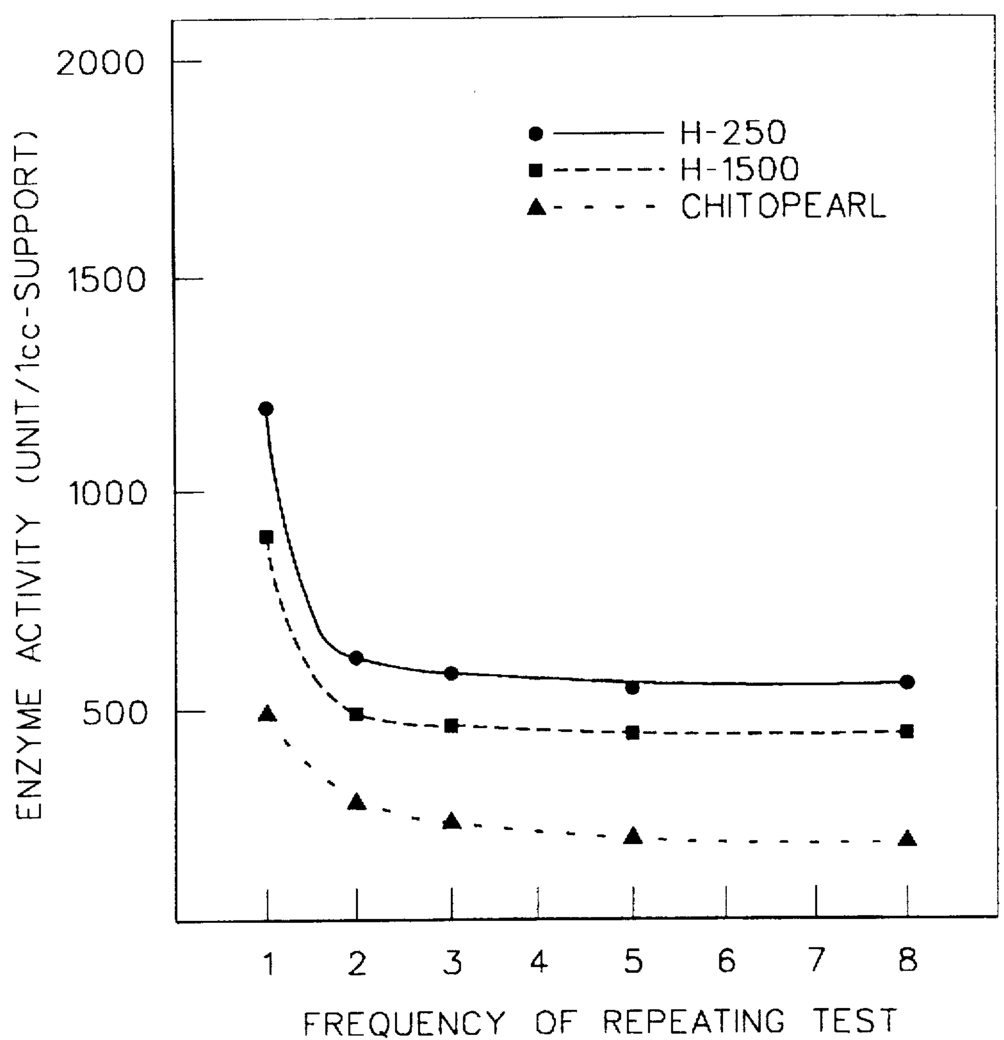
FIG. 7 is a graphical representation which shows the relation between the frequency of repeating test and the enzyme activity with respect to various carriers produced by the embodiments 4 and 5, and the comparative example.

The carrier sample was suffered from a silane coupling agent and glutaraldehyde in the same manner as Embodiment 4, and then immobilized with enzyme. This enzyme immobilized sample was subjected to the measurement of enzyme activity. On the same occasion, a comparative sample was prepared in the same manner as Embodiment 4 by using a typically used commercial available carrier, Chitopearl, chitosan beads having an average particle diameter of 1000 μm, for immobilizing enzyme. It is well known that Chitopearl has an excellent capability of generating enzyme activity. Also this comparative sample was subjected to the measurement of enzyme activity under the same condition as above. The resulted data is shown in FIG. 7. The data shows the comparative effects among the sample H-1500 according to Embodiment 5, the sample H-250 according to Embodiment 3, and Chitopearl as the comparative sample. Although the enzyme activity of the sample H-1500 is slightly lower than that of the sample H-250, it is about twice as Chitopearl which has been believed to have an excellent capability of generating enzyme activity. As a result, the method of the present invention may increase the particle size of the carrier particle to overcome the problem caused by the pressure loss owing to the high viscous reactant. For example, even when the average particle diameter is so large as 1500 μm, the carrier produced by the method according to the present invention can generate a practically available enzyme activity and have a relatively lower pressure loss. Accordingly, these results means that the particle diameter having several mm can be practically used.

As disclosed above, the porous powder adapted for a porous carrier to immobilize enzyme is produced by adding a strong acid to kaolin mineral, applying a hydrothermal treatment and a baking treatment to form the porous powder having a uniform pore distribution and a high pore ratio adapted for the porous carrier to immobilize enzyme. Alternatively, the method to produce the objective porous powder includes a first step for adding a strong acid to kaolin mineral, a second step for applying a hydrothermal treatment to the resulted material from the first step, a third step for granulating the slurry or powder resulted from the second step to form granular materials, and a fourth step for baking the granular materials under predetermined conditions to form the porous powder having a uniform pore distribution and a high pore ratio adapted for the porous carrier to immobilize enzyme.

In the method according to the present invention, the strong acid treatment ensures to provide chemical stability, and both the hydrothermal and baking treatments ensure to provide thermal stability and realize a porous carrier manufacturing process with an economical profit. The required pore amount can be formed in accordance with the baking temperature.

In addition to the above advantages, the method does not break the sepiolite crystal and completely remove alkaline impurities from the sepiolite carrier, so that the inherent properties of the kaolin mineral can be effectively utilized in practical uses.

As many apparently widely different embodiments of this invention may be made without departing from the spirit and scope thereof, it is to be understood that the invention is not limited to the specific embodiments thereof as defined in the appended claims.

What is claimed is:

1. Method of preparing an enzyme immobilizing carrier, comprising the steps of:

a) providing a material consisting essentially of kaolin mineral;

b) subjecting the material to acid treatment with a strong acid having a pH of 4.0 or less, and hydrothermal treatment at a temperature of from about 100° C. to about 250° C.;

c) drying the material from step b) and thereby producing a porous powder; and d) baking the porous powder at a temperature of from about 350° C. to about 1000° C. and thereby producing the carrier.

2. The method of claim 1, including the step of:

a) surface treating the carrier with a silane coupling agent and glutaraldehyde.

3. The method of claim 1, including the step of:

a) prior to said drying step, preparing a slurry from the material resulting from said acid and hydrothermal treatments.

4. The method of claim 3, including the step of:

a) prior to preparing the slurry, washing the material resulting from said acid and hydrothermal treatments.

5. The method of claim 1, including the step of:

a) selecting the kaolin mineral from natural and synthetic minerals chosen from the group consisting of kaolinite, dickite, nacrite, and halloysite.

6. The method of claim 5, including the step of:

a) selecting as the strong acid an acid chosen from the group consisting of inorganic acids and organic acids.

7. The method of claim 5, including the step of:

a) performing said hydrothermal treatment at a temperature of at least 100° C. and for a period of no less than one hour.

8. The method of claim 7, including the step of:

a) performing said hydrothermal treatment at a temperature falling within the range of 120° C. to 200° C.

9. The method of claim 3, including the step of:

a) forming the slurry from granular material having a particle diameter in excess of 10 μm.

10. The method of claim 3, including the step of:

a) transforming the slurry into a granular material by a granulation method chosen from the group consisting of rotary granulation, spray dry granulation, stirring granulation, vacuum dry granulation, and flowing layer granulation.

* * * * *